United States Patent [19]
Chen et al.

[11] Patent Number: 5,638,820
[45] Date of Patent: Jun. 17, 1997

[54] ULTRASOUND SYSTEM FOR ESTIMATING THE SPEED OF SOUND IN BODY TISSUE

[75] Inventors: Jian-Feng Chen, Issaquah; Lin-Xin Yao; Patrick L. Von Behren, both of Bellevue, all of Wash.

[73] Assignee: Siemens Medical Systems, Inc., Iselin, N.J.

[21] Appl. No.: 674,652

[22] Filed: Jun. 25, 1996

[51] Int. Cl.⁶ .................................................. A61B 8/00
[52] U.S. Cl. ........................... 128/660.02; 128/660.06
[58] Field of Search .................... 128/660.01, 660.02, 128/660.04, 660.06, 660.07, 661.02

[56] References Cited

U.S. PATENT DOCUMENTS

| | | | |
|---|---|---|---|
| 4,361,154 | 11/1982 | Pratt, Jr. | 128/660.01 |
| 5,218,963 | 6/1993 | Mazess | 128/660.06 |
| 5,349,959 | 9/1994 | Wiener et al. | 128/660.06 |

*Primary Examiner*—George Manuel

[57] ABSTRACT

An ultrasound system (50) estimates the speed of sound in the tissue (60) under examination. The ultrasound system obtains a series of test images (150) using different estimates of the speed of sound in the body tissue. For each image produced, the ultrasound system computes a function that is indicative of image quality for one or more regions of interest (152) in the test image. The image quality function exhibits a minimum or maximum when computed for a region of interest obtained at a speed of sound substantially equal to a true speed of sound in the tissue. The ultrasound system selects the test image having the minimum or maximum function value and obtains subsequent images of the tissue using the speed of sound used to obtain the test image selected.

12 Claims, 2 Drawing Sheets

ULTRASOUND SYSTEM FOR ESTIMATING THE SPEED OF SOUND IN BODY TISSUE

FIELD OF THE INVENTION

The present invention relates to ultrasound systems in general, and in particular to methods for improving the quality of ultrasound images.

BACKGROUND OF THE INVENTION

Ultrasound is an increasingly used tool for noninvasively examining a patient's body. A typical ultrasound system works by transmitting high frequency acoustic signals into the body and detecting and analyzing the returned echoes. To create an image of the tissue in the body, the strength of the ultrasound echo is determined and used to modify the intensity of pixels in a digital display screen.

For reasons set forth below, the resolution with which the internal body matter can be imaged is highly dependent upon the speed at which the ultrasonic pulses travel in the body. The speed of sound is known to vary with tissue type. For example, the speed of sound in fat tissue varies between 1410 and 1479 m/sec., while in liver tissue the speed of sound varies between 1553 and 1607 m/sec. For kidney tissue, the speed of sound varies between 1558 and 1568 m/sec., while in muscle tissue, the speed of sound varies between 1543 and 1631 m/sec.

In conventional ultrasound systems, the speed of sound is pre-set to be approximately 1540 m/sec. and cannot be changed. While this estimate provides fairly clear images, the image resolution can be improved by refining the speed of sound estimate. Because the tissue under examination may not be homogenous, and because the speed may vary within tissues of the same type, there is no way of preprogramming the optimum speed prior to examination of the tissue. Therefore, there is a need for an ultrasound system that can automatically estimate the speed of sound in the tissue under examination in order to increase the resolution of an ultrasound image.

SUMMARY OF THE INVENTION

The present invention comprises a method and apparatus for estimating the speed of ultrasonic signals in a tissue sample. The ultrasound system produces a series of test images, each of which is obtained assuming a different speed of sound. For each test image produced, a predetermined region of interest is selected and a mathematical calculation that is indicative of the image quality in the regional interest is computed. The mathematical calculation exhibits a minimum or maximum when the speed of sound is optimized. Therefore, the computer system selects the test image associated with the region of interest where the mathematical calculation produces the minimum or maximum to determine the speed of sound in the tissue. Subsequent images produced by the ultrasound system are obtained using the speed of sound determined. In the presently preferred embodiment of the invention, the mathematical calculation is a second-order statistical parameter such as a spatial correlation function computed for the pixels in the region of interest.

The speed of sound estimation as determined by the test image selected can also be used to quantitatively analyze the tissue under examination. By calculating the speed of sound and comparing the result with the speed of sound in known tissue samples, the ultrasound system can characterize the type of tissue under examination.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As indicated above, the present invention is a method and apparatus for determining an optimum speed of sound within a tissue sample in order to improve the resolution of an ultrasound image.

Figure 1:
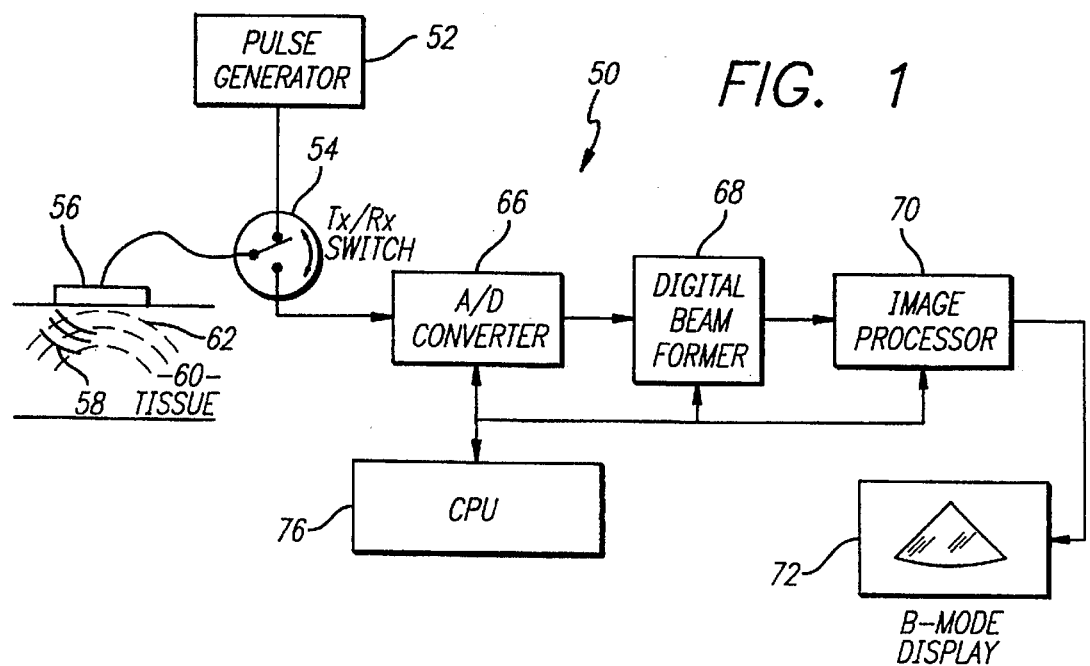
FIG. 1 is a simplified block diagram of an ultrasound imaging system according to the present invention.

FIG. 1 is a simplified block diagram of an ultrasound system according to the present invention. The ultrasound system 50 includes a pulse generator 52 that generates a series of electronic signals that are optimized to produce echoes that can be detected and converted into an ultrasound image. The output of the pulse generator 52 is fed to a transmit/receive switch 54 that has two positions. In the first position, the output of the pulse generator is coupled to an ultrasonic transducer 56. In the second position, the signals produced by the transducer in response to a received echo are coupled to an analog-to-digital converter 66.

The ultrasonic transducer 56 comprises an array of transducer elements, each of which is a piezoelectric crystal that converts the electronic signal into an ultrasonic wave 58 that is directed into a patient's body tissue 60. An ultrasound echo 62 is reflected off the internal body matter of the patient and is received by the ultrasonic transducer 56. Upon receiving the ultrasound echo, the transducer elements generate electronic signals that are analyzed by the ultrasound system to produce the ultrasound image.

With the transmit/receive switch 54 in the second position, the output signals produced by the ultrasonic transducer 56 are coupled to the analog-to-digital converter 66. The analog-to-digital converter converts the received echoes from a continuous analog signal to a discrete digital signal. The output of the analog-to-digital converter 66 is fed to a digital beam former 68 that combines the digitized signals from each of the transducer elements in the transducer into a single binary number that is representative of the echo intensity at any given position in the body tissue. The output of the digital beam former is fed to an image processor 70 which produces a digital ultrasound image that is in turn displayed on a display screen 72.

Controlling the operation of the ultrasound system 50 is a central processing unit 76 having its own internal memory in which data and the operating instructions for the CPU are stored. In addition, the CPU may be coupled to a mass storage device such as a hard drive, a communication circuit for transmitting and receiving data from a remote location and a video tape recorder for recording the ultrasound images produced.

Figure 2:
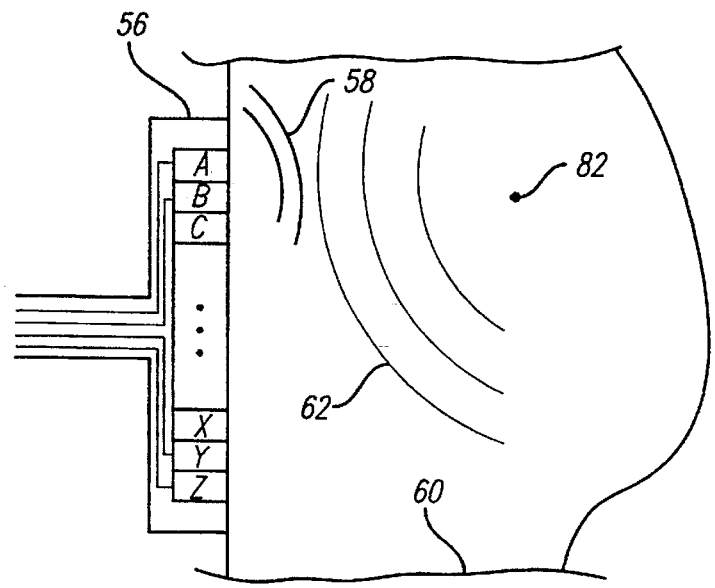
FIG. 2 is a diagram illustrating how an ultrasound echo is created in body tissue.

FIG. 2 illustrates in greater detail how an ultrasound image is constructed. As indicated above, the ultrasonic transducer 56 comprises a number (usually 128 or 256) of piezoelectric transducer elements that are labeled for purposes of illustration as elements ABC . . . XYZ. A small subset of the transducer elements are triggered to convert the electronic signals produced by the pulse generators into ultrasonic sound waves 58 that travel into the patient's tissue 60. The ultrasonic sound waves are reflected off the body matter and travel back toward the ultrasonic transducer 58 as an ultrasonic echo 62.

Because the orientation of the ultrasound transducer 56 is not always symmetric with respect to the source of the echo, the echo does not reach all transducer elements at the same time. For example, a point 82 in the tissue reflects a portion of the incoming ultrasonic wave back toward the ultrasonic transducer. Due to the orientation of the transducer 56 with respect to the point 82 in the tissue, the wave front of the reflected echo 62 will reach the transducer elements A, B, and C before reaching the transducer elements X, Y, and Z. In order to create the best possible image of the point 82, it is necessary that an electronic signal produced by each of the transducer elements be sampled as close as possible to the time at which the wave front of the reflected echo reaches the individual transducer element. The process of determining when to sample the output signals of the transducer elements is referred to as "beam forming" and is performed by the digital beam former 68 shown in FIG. 1 according to the techniques well known in the art.

Figure 3:
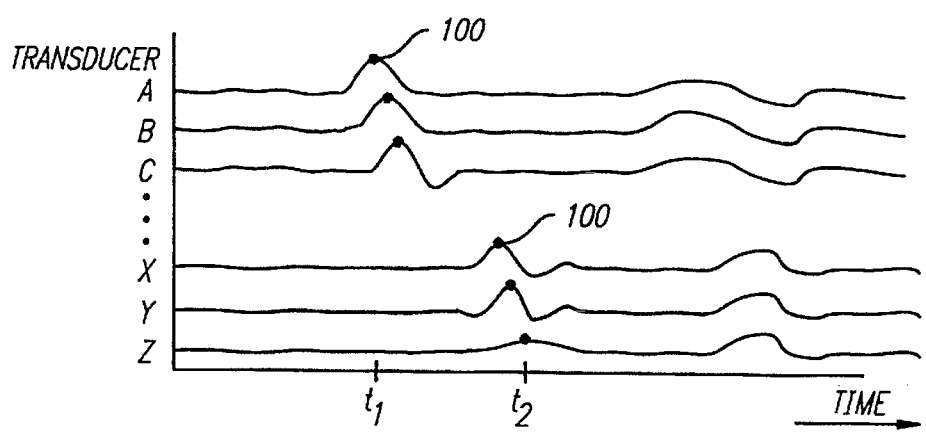
FIG. 3 is a graph showing the signals produced by a plurality of ultrasound transducer elements in response to a received ultrasound echo.

FIG. 3 is a representative graph of the output signals produced by the transducer elements ABC . . . XYZ of the ultrasonic transducer in response to a received echo. A peak 100 represents the electronic signal produced in response to the wavefront of the echo from the point 82 shown in FIG. 2. As can be seen, the peak 100 is produced by transducer element A at a time $t_1$, while the peak 100 is produced by the transducer element Z at a later time $t_2$ because the transducer element Z is farther away from the source of the echo.

In order to produce the best image of the point 82, it is necessary that the output signals of the transducers be sampled such that it appears as if each of the transducer elements were equidistant to the source of the echo. For the example shown in FIG. 3, the output signal produced by the transducer element A should be sampled as closely as possible to the time $t_1$, while the output signals of the transducer element Z should be sampled as close as possible to the time $t_2$. The digital beam former 68 is programmed to calculate the time at which the output signals of the transducer elements are sampled as a function of the depth in the tissue being imaged and an expected speed of sound in the tissue.

As will be apparent to those skilled in the art, the time at which each of the output signals produced by transducer elements are sampled is highly dependent upon the speed at which ultrasonic echoes travel through in the tissue under examination. As described above, most ultrasound systems preset the speed of sound in tissue to be approximately 1540 m/sec. However, for many types of tissue, this estimate may be off by as much as 5–8%. Therefore, the ultrasound system of the present invention seeks to refine the speed of sound estimation for the tissue under examination in order to improve the quality of the ultrasonic image produced.

Figure 4:
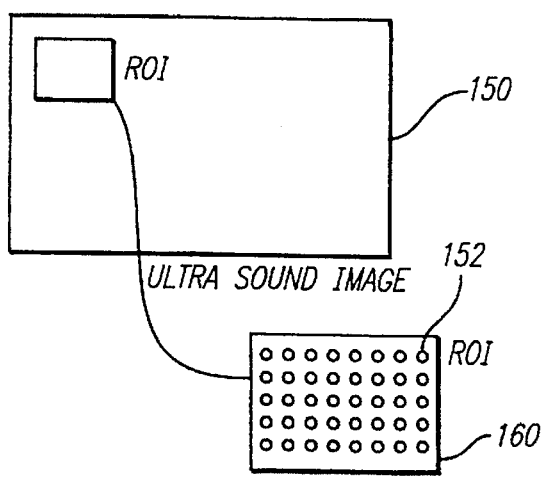
FIG. 4 illustrates how a region of interest in an ultrasound test image is selected to optimize the speed of sound estimation.
Figure 5A:
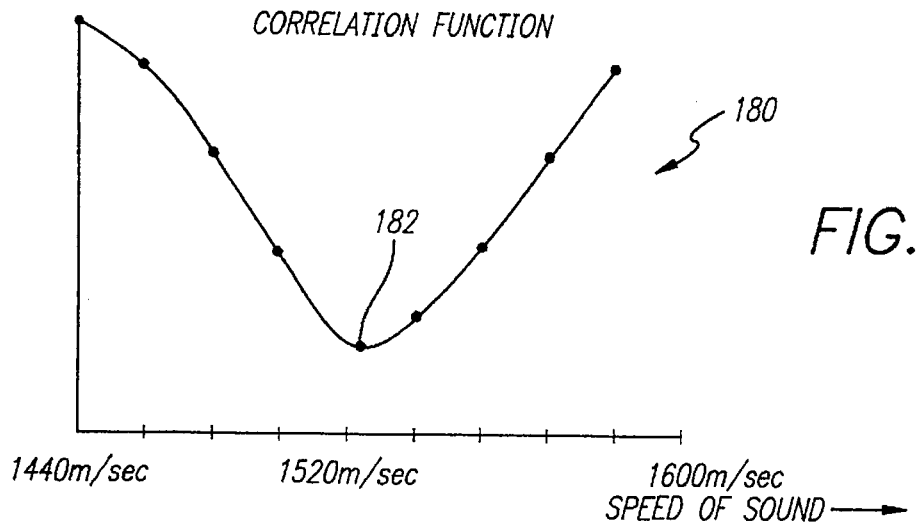
FIGS. 5A and 5B are graphs showing how the mathematical functions calculated for the pixels in the region of interest vary with different speed of sound estimations.
Figure 5B:
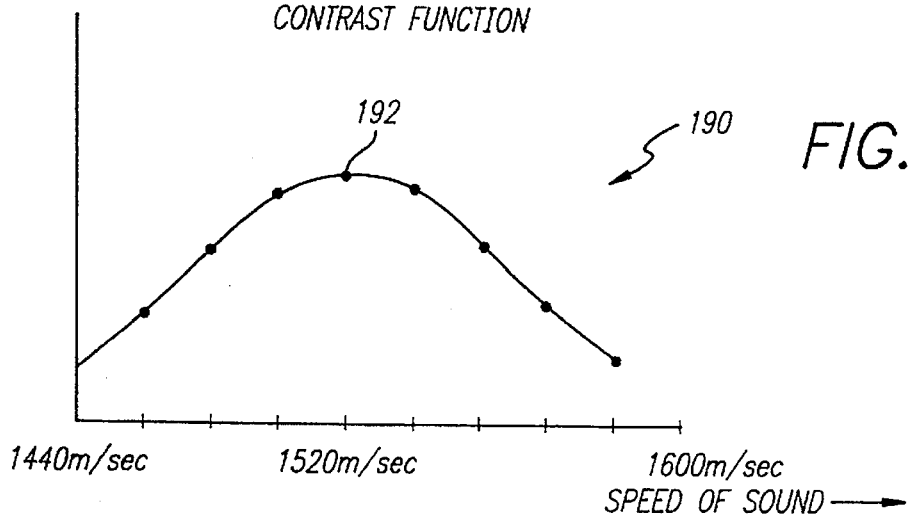

FIGS. 4 and 5A–5B illustrate how the present invention operates to estimate the speed of sound in a tissue sample under examination. To begin, the ultrasound system obtains a number of test images, each of which assumes a different speed of sound. For each test image, the beam former is programmed with an estimated speed of sound and the test image is obtained. In the presently preferred embodiment of the invention, test images are obtained beginning with a speed of sound equal to 1440 m/sec. and increasing in increments of 20 m/sec. up to a speed of 1600 m/sec. Each test image obtained is stored in the CPU's memory.

After all the test images have been obtained, the CPU analyzes the test images to select the one having the best image quality. Because the best image quality is obtained when the estimated speed of sound is nearly equal to the true speed of sound in the tissue under examination, the test image with the best quality indicates the speed of sound in the tissue.

FIG. 4 represents one of the test images obtained using an assumed speed of sound. The test image 150 comprises a number of pixels 152, each having a brightness that is dependent upon the strength of the received echo produced by a corresponding point within the tissue under examination. For each test image, a region of interest 160 is selected. Typically, the region of interest comprises an area of 50×50 pixels. However, other region sizes could be used if desired.

To compute the speed of sound in the tissue, the second-order statistical parameters are calculated on the pixels found within the region of interest. In the presently preferred embodiment of the invention, the spatial correlation of the pixel gray value is computed according to the equation:

$$R_d = \frac{\sum_{k=1}^{M} \sum_{i=1}^{i=N-d} I_{ik} I_{jk}}{<I>^2} - 1.0 \quad (1)$$

for a region of interest having M by N pixels where I is the gray value of the pixel, (I) is the mean gray value computed over the region of interest and d is the distance between pixels. In the presently preferred embodiment of the invention, d is selected between 1 and 10. The calculation according to Equation 1 is computed for the same region of interest in each of the test images. The results of the computations are stored in the memory of the CPU for analysis.

FIG. 5A is a representative graph 180 of the spatial correlation function specified in Equation 1 for a series of test images obtained with varying speed of sound estimates. The spatial correlation function has a minimum that occurs at a point 182 that is substantially equal to the optimal speed of sound in the tissue. Therefore, to select the best estimate of the speed of sound, the ultrasound system selects the test image having the minimum spatial correlation function computed on the region of interest. The speed of sound used to obtain the selected test image is therefore chosen as the optimum speed of sound for subsequent images of the tissue under examination.

A more general form of equation 1 is:

$$\text{Correlation} = \sum_{\substack{k=1 \\ l=k+d_2}}^{k=M-d_2} \sum_{\substack{i=1 \\ j=i+d_1}}^{i=N-d_1} (I_{ij} - <I>)(I_{kl} - <I>) \quad (2)$$

where $d_1$ and $d_2$ are the distance between pixels. Preferably $d_1$ is selected between 1 and 10 and $d_2$ is 0. However, $d_2$ may also be selected between 1 and 10 if less sensitivity is desired.

As an alternative to the correlation functions set forth in Equations 1 and 2, a contrast function according to the following equation could also be used:

$$\text{Contrast} = \sum_{\substack{k=1 \\ l=k+d_2}}^{k=M-d_2} \sum_{\substack{i=1 \\ j=i+d_1}}^{i=N-d_1} (I_{ij} - I_{kl})^2 \qquad (3)$$

The contrast function exhibits a maximum when computed for an image obtained at the true speed of sound in the tissue. FIG. 5B is a graph 190 showing the results of Equation 3 computed for the region of interest of the test images obtained assuming various speed of sound estimates. The graph exhibits a maximum at a point 192 where the estimated speed of sound is closest to the true speed of sound in the tissue. Therefore, to determine the speed of sound using Equation 3, the test image that produces the maximum value when computed for the regional interest is selected. The speed of sound used to obtain the test image selected is therefore used as the optimum speed of sound by the beam formed in obtaining subsequent images of the tissue under examination.

In the presently preferred embodiment of the invention, approximately nine test images are obtained using estimates of the speed of sound that increase in 20 m/sec. increments. However, it will be appreciated that additional test images can be obtained using estimates near the optimal speed of sound or interpolation techniques can be used to further refine the speed of sound estimate.

Figure 6:
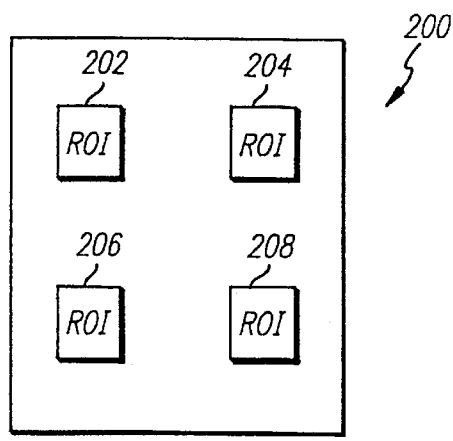
FIG. 6 illustrates how the speed of sound may be determined for more than one region of interest.

The technique of the present invention can also be used where the tissue under examination is non-homogeneous. By analyzing more than one region of interest in the test images, the speed of sound may be found to vary within the tissue. This situation is illustrated in FIG. 6 whereby a test image 200 is obtained having four regions of interest 202, 204, 206 and 208. The beam former is programmed to adjust the estimated speed of sound for each region of interest. A series of test images is obtained and the CPU calculates the second order statistical parameters described above to determine the speed of sound for each region of interest. The quality of subsequent images of the tissue can be improved by programming the beam former "on the fly" with the appropriate speed of sound determined for a particular region of interest. As will be appreciated, the number of test images required to determine the speed of sound in more than one region of interest increases with each region of interest added.

Finally, the present invention is also useful for qualitatively characterizing the type of tissue under examination. By estimating the speed of sound from the received image and comparing the estimated speed of sound with known data concerning the speed of sound in various types of tissue, the ultrasound system can characterize what type of tissue is under examination. For example, it may be advantageous to display different types of tissue in different colors or to delineate the transition regions between various types of tissue based on the speed of sound determined for the different tissue regions.

The embodiments of the invention in which an exclusive property or privilege is claimed are defined as follows:

1. A method for use in an imaging ultrasound system of the type wherein an ultrasound image is displayed as an array of variable intensity pixels, the method for determining the speed of sound in a tissue sample under examination comprising the steps of:

obtaining a number of test images of the tissue, wherein each test image uses an estimate of the speed of sound;

for each test image obtained, selecting a number of pixels that comprise a region of interest;

computing a function that is indicative of the image quality for the pixels that comprise the region of interest;

selecting an image from the number of test images based on a result of the function computed for each region of interest and selecting as the speed of sound in the tissue under examination the estimated speed of sound used to obtain the test image selected; and displaying an ultrasound image obtained with the speed of sound determined.

2. The method of claim 1, wherein the function computed for each region of interest is a second-order statistical parameter having a minimum when computed for an image obtained with a speed of sound substantially equal to a true speed of sound in the tissue, wherein the step of selecting an image from the number of test images further comprises the steps of:

comparing a series of results for the function computed for the region of interest in each test image; and selecting the test image that produced a minimum function result.

3. The method of claim 2, wherein the function computed for each region of interest is a correlation function.

4. The method of claim 1, wherein the function computed for each region of interest is a second-order statistical parameter having a maximum when computed for an image obtained with a speed of sound substantially equal to a true speed of sound in the tissue, wherein the step of selecting an image from the number of test images further comprises the steps of:

comparing a series of results for the function computed for the region of each test image; and selecting the test image having the region of interest that produced a maximum function result.

5. The method of claim 4, wherein the function computed for each region of interest is a contrast function.

6. The method of claim 1, further comprising the steps of:

comparing the speed of sound determined for the tissue under examination with speed of sound in known tissue types; and providing an indication of the type of tissue under examination based on the speed of sound comparison.

7. An ultrasound imaging system for characterizing a speed of sound in a tissue sample under examination, comprising:

a digital beam former that is programmed to obtain a number of test images of the tissue, wherein each test image is obtained using an estimate of the speed of sound in the tissue;

a central processing unit that selects a number of pixels that comprise a region of interest in each test image;

wherein the central processing unit computes a function that is indicative of the image quality for the pixels that comprise the region of interest, selects an image from the number of test images based on a result of the function computed for each region of interest and determines the speed of sound in the tissue under examination as the speed of sound used to obtain the test image selected, the digital beam former being programmed with the determined speed of sound to obtain subsequent images of the tissue under examination.

8. The ultrasound system of claim 7, wherein the central processing unit programs the digital beam former with a different estimate of the speed of sound for each test image obtained.

9. The ultrasound system of claim 7, wherein the function that is indicative of the image quality in the region of interest is a second-order statistical parameter that exhibits a minimum when computed for an image obtained with a speed of sound substantially equal to a true speed of sound in the tissue.

10. The ultrasound system of claim 9, wherein the function is a correlation function.

11. The ultrasound system of claim 8, wherein the function that is indicative of the image quality in the region of interest is a second order statistical parameter that exhibits a maximum when computed for an image obtained with a speed of sound substantially equal to a true speed of sound in the tissue.

12. The ultrasound system of claim 8, wherein the function is a contrast function.

* * * * *